(12) United States Patent
Averbuch et al.

(10) Patent No.: US 10,674,970 B2
(45) Date of Patent: *Jun. 9, 2020

(54) METHODS AND SYSTEMS FOR USING MULTI VIEW POSE ESTIMATION

(71) Applicant: Body Vision Medical Ltd., Ramat Hasharon (IL)

(72) Inventors: Dorian Averbuch, Ramat Hasharon (IL); Eliron Amir, Kfar Saba (IL); Dima Sezganov, Petah Tikva (IL); Eyal Cohen, Petah Tikva (IL)

(73) Assignee: Body Vision Medical Ltd., Ramat Hasharon (IL)

( * ) Notice: Subject to any disclaimer, the term of this patent is extended or adjusted under 35 U.S.C. 154(b) by 518 days.

This patent is subject to a terminal disclaimer.

(21) Appl. No.: 15/456,130

(22) Filed: Mar. 10, 2017

(65) Prior Publication Data

US 2017/0258418 A1 Sep. 14, 2017

Related U.S. Application Data

(60) Provisional application No. 62/306,502, filed on Mar. 10, 2016, provisional application No. 62/407,720, filed on Oct. 13, 2016.

(51) Int. Cl.
*A61B 6/12* (2006.01)
*A61B 6/00* (2006.01)
(Continued)

(52) U.S. Cl.
CPC .......... *A61B 6/12* (2013.01); *A61B 6/485* (2013.01); *A61B 6/487* (2013.01); *A61B 6/488* (2013.01);
(Continued)

(58) Field of Classification Search
CPC .......... A61B 6/032; A61B 6/12; A61B 6/485; A61B 6/487; A61B 6/488; A61B 6/50;
(Continued)

(56) References Cited

U.S. PATENT DOCUMENTS

2008/0262342 A1* 10/2008 Averbruch ............ A61B 6/12
600/424
2013/0293578 A1* 11/2013 Leung ................ G06F 3/147
345/633

(Continued)

OTHER PUBLICATIONS

Bernhardt, Sylvain, et al. "Automatic detection of endoscope in intraoperative ct image: Application to ar guidance in laparoscopic surgery." 2014 IEEE 11th International Symposium on Biomedical Imaging (ISBI). IEEE, 2014. (Year: 2014).*

*Primary Examiner* — Pinalben Patel
(74) *Attorney, Agent, or Firm* — Greenberg Traurig, LLP

(57) ABSTRACT

The present invention is disclosing several methods related to intra-body navigation of radiopaque instrument through natural body cavities. One of the methods is disclosing the pose estimation of the imaging device using multiple images of radiopaque instrument acquired in the different poses of imaging device and previously acquired imaging. The other method allows to resolve the radiopaque instrument localization ambiguity using several approaches, such as radiopaque markers and instrument trajectory tracking.

6 Claims, 6 Drawing Sheets

(51) Int. Cl.
*G06T 7/33* (2017.01)
*G06T 7/73* (2017.01)
*A61B 6/03* (2006.01)

(52) U.S. Cl.
CPC .............. *A61B 6/50* (2013.01); *A61B 6/5211* (2013.01); *A61B 6/5235* (2013.01); *G06T 7/344* (2017.01); *G06T 7/75* (2017.01); *A61B 6/032* (2013.01); *G06T 2207/10064* (2013.01); *G06T 2207/10081* (2013.01); *G06T 2207/10132* (2013.01); *G06T 2207/30061* (2013.01); *G06T 2207/30172* (2013.01)

(58) Field of Classification Search
CPC ................ A61B 6/5211; A61B 6/5235; A61B 2090/365; A61B 34/20; A61B 17/00234; A61B 17/3478; A61B 1/00149; A61B 2034/2048; A61B 34/30; A61B 5/061; A61B 8/0841; A61B 8/12; A61B 90/06; A61B 90/361; A61B 2090/363; A61N 5/1039; G06T 19/00; G06T 2207/20101; G06T 2207/30101; G06T 7/187; G06T 7/337; G06T 7/38
See application file for complete search history.

(56) References Cited

U.S. PATENT DOCUMENTS

2016/0120521 A1\* 5/2016 Weingarten .......... A61B 6/5235
600/424
2019/0325645 A1\* 10/2019 Guendel ............... G06T 11/001

\* cited by examiner

METHODS AND SYSTEMS FOR USING MULTI VIEW POSE ESTIMATION

CROSS REFERENCE TO RELATED APPLICATION

This application claims priority to U.S. Provisional Application Ser. No. 62/306,502, filed on Mar. 10, 2016, entitled "METHODS AND SYSTEMS FOR USING MULTI VIEW POSE ESTIMATION" and U.S. Provisional Application Ser. No. 62/407,720 filed on Oct. 13, 2016, entitled "METHODS AND SYSTEMS FOR USING MULTI VIEW POSE ESTIMATION" the entire contents of which are hereby incorporated by reference in their entireties.

FIELD OF THE INVENTION

The embodiments of the present invention relate to interventional devices and methods of use thereof.

BACKGROUND OF INVENTION

Use of minimally invasive procedures such as endoscopic procedures, video-assisted thoracic surgery, or similar medical procedures can be used as diagnostic tool for suspicious lesions or as treatment means for cancerous tumors.

SUMMARY OF INVENTION

In some embodiments, the present invention provides a method, comprising:
  obtaining a first image from a first imaging modality,
  extracting at least one element from the first image from the first imaging modality, wherein the at least one element comprises an airway, a blood vessel, a body cavity, or any combination thereof;
  obtaining, from a second imaging modality, at least (i) a first image of a radiopaque instrument in a first pose and (ii) a second image of the radiopaque instrument in a second pose,
    wherein the radiopaque instrument is in a body cavity of a patient;
  generating at least two augmented bronchograms,
    wherein a first augmented bronchogram corresponds to the first image of the radiopaque instrument in the first pose, and
    wherein a second augmented bronchogram corresponds to the second image of the radiopaque instrument in the second pose,
  determining mutual geometric constraints between:
    (i) the first pose of the radiopaque instrument, and
    (ii) the second pose of the radiopaque instrument,
  estimating the first pose of the radiopaque instrument and the second pose of the radiopaque instrument by comparing the first pose of the radiopaque instrument and the second pose of the radiopaque instrument to the first image of the first imaging modality,
    wherein the comparing is performed using:
      (i) the first augmented bronchogram,
      (ii) the second augmented bronchogram, and
      (iii) the at least one element, and
    wherein the estimated first pose of the radiopaque instrument and the estimated second pose of the radiopaque instrument meets the determined mutual geometric constraints,
  generating a third image; wherein the third image is an augmented image derived from the second imaging modality which highlights an area of interest,
    wherein the area of interest is determined from data from the first imaging modality.

In some embodiments, the at least one element from the first image from the first imaging modality further comprises a rib, a vertebra, a diaphragm, or any combination thereof.
In some embodiments, the mutual geometric constraints are generated by:
  a. estimating a difference between (i) the first pose and (ii) the second pose by comparing the first image of the radiopaque instrument and the second image of the radiopaque instrument,
    wherein the estimating is performed using a device comprising a protractor, an accelerometer, a gyroscope, or any combination thereof, and wherein the device is attached to the second imaging modality;
  b. extracting a plurality of image features to estimate a relative pose change,
    wherein the plurality of image features comprise anatomical elements, non-anatomical elements, or any combination thereof,
    wherein the image features comprise: patches attached to a patient, radiopaque markers positioned in a field of view of the second imaging modality, or any combination thereof,
    wherein the image features are visible on the first image of the radiopaque instrument and the second image of the radiopaque instrument;
  c. estimating a difference between (i) the first pose and (ii) the second pose by using a at least one camera,
    wherein the camera comprises: a video camera, an infrared camera, a depth camera, or any combination thereof,
    wherein the camera is at a fixed location,
    wherein the camera is configured to track at least one feature,
      wherein the at least one feature comprises: a marker attached the patient, a marker attached to the second imaging modality, or any combination thereof, and
      tracking the at least one feature;
  d. or any combination thereof.

In some embodiments, the method further comprises: tracking the radiopaque instrument for: identifying a trajectory, and using the trajectory as a further geometric constraint, wherein the radiopaque instrument comprises an endoscope, an endo-bronchial tool, or a robotic arm.

In some embodiments, the present invention is a method, comprising:
  generating a map of at least one body cavity of the patient,
    wherein the map is generated using a first image from a first imaging modality, obtaining, from a second imaging modality, an image of a radiopaque instrument comprising at least two attached markers,
    wherein the at least two attached markers are separated by a known distance, identifying a pose of the radiopaque instrument from the second imaging modality relative to a map of at least one body cavity of a patient,
  identifying a first location of the first marker attached to the radiopaque instrument on the second image from the second imaging modality,
  identifying a second location of the second marker attached to the radiopaque instrument on the second image from the second imaging modality, and measuring a distance between the first location of the first marker and the second location of the second marker, projecting the known distance between the first marker and the second marker, comparing the measured distance with the projected known distance between the first marker and the second marker to identify a specific location of the radiopaque instrument inside the at least one body cavity of the patient.

In some embodiments, the radiopaque instrument comprises an endoscope, an endo-bronchial tool, or a robotic arm.

In some embodiments, the method further comprises: identifying a depth of the radiopaque instrument by use of a trajectory of the radiopaque instrument.

In some embodiments, the first image from the first imaging modality is a pre-operative image. In some embodiments, the at least one image of the radiopaque instrument from the second imaging modality is an intra-operative image.

In some embodiments, the present invention is a method, comprising:

obtaining a first image from a first imaging modality, extracting at least one element from the first image from the first imaging modality,
wherein the at least one element comprises an airway, a blood vessel, a body cavity or any combination thereof;

obtaining, from a second imaging modality, at least (i) a one image of a radiopaque instrument and (ii) another image of the radiopaque instrument in two different poses of second imaging modality
wherein the first image of the radiopaque instrument is captured at a first pose of second imaging modality,
wherein the second image of the radiopaque instrument is captured at a second pose of second imaging modality, and
wherein the radiopaque instrument is in a body cavity of a patient;

generating at least two augmented bronchograms correspondent to each of two poses of the imaging device,
wherein a first augmented bronchogram derived from the first image of the radiopaque instrument and the second augmented bronchogram derived from the second image of the radiopaque instrument, determining mutual geometric constraints between:
(i) the first pose of the second imaging modality, and
(ii) the second pose of the second imaging modality, estimating the two poses of the second imaging modality relatively to the first image of the first imaging modality, using the correspondent augmented bronchogram images and at least one element extracted from the first image of the first imaging modality;
wherein the two estimated poses satisfy the mutual geometric constrains.

generating a third image; wherein the third image is an augmented image derived from the second imaging modality highlighting the area of interest, based on data sourced from the first imaging modality.

In some embodiments, anatomical elements such as: a rib, a vertebra, a diaphragm, or any combination thereof, are extracted from the first imaging modality and from the second imaging modality.

In some embodiments, the mutual geometric constraints are generated by:

a. estimating a difference between (i) the first pose and (ii) the second pose by comparing the first image of the radiopaque instrument and the second image of the radiopaque instrument,
wherein the estimating is performed using a device comprising a protractor, an accelerometer, a gyroscope, or any combination thereof, and
wherein the device is attached to the second imaging modality;

b. extracting a plurality of image features to estimate a relative pose change,
wherein the plurality of image features comprise anatomical elements, non-anatomical elements, or any combination thereof,
wherein the image features comprise: patches attached to a patient, radiopaque markers positioned in a field of view of the second imaging modality, or any combination thereof,
wherein the image features are visible on the first image of the radiopaque instrument and the second image of the radiopaque instrument;

c. estimate a difference between (i) the first pose and (ii) the second pose by using a at least one camera,
wherein the camera comprises: a video camera, an infrared camera, a depth camera, or any combination thereof,
wherein the camera is at a fixed location,
wherein the camera is configured to track at least one feature,
wherein the at least one feature comprises: a marker attached the patient, a marker attached to the second imaging modality, or any combination thereof, and
tracking the at least one feature;

d. or any combination thereof.

In some embodiments, the method further comprises tracking the radiopaque instrument to identify a trajectory and using such trajectory as additional geometric constrains, wherein the radiopaque instrument comprises an endoscope, an endo-bronchial tool, or a robotic arm.

In some embodiments, the present invention is a method to identify the true instrument location inside the patient, comprising:

using a map of at least one body cavity of a patient generated from a first image of a first imaging modality, obtaining, from a second imaging modality, an image of the radiopaque instrument with at least two markers attached to it and having the defined distance between them, that may be perceived from the image as located in at least two different body cavities inside the patient, obtaining the pose of the second imaging modality relative to the map identifying a first location of the first marker attached to the radiopaque instrument on the second image from the second imaging modality, identifying a second location of the second marker attached to the radiopaque instrument on the second image from the second imaging modality, and measuring a distance between the first location of the first marker and the second location of the second marker.

projecting the known distance between markers on each of the perceived location of the radiopaque instrument using the pose of the second imaging modality comparing the measured distance to each of projected distances between the two markers to identify the true instrument location inside the body.

In some embodiments, the radiopaque instrument comprises an endoscope, an endo-bronchial tool, or a robotic arm.

In some embodiments, the method further comprises: identifying a depth of the radiopaque instrument by use of a trajectory of the radiopaque instrument.

In some embodiments, the first image from the first imaging modality is a pre-operative image. In some embodiments, the at least one image of the radiopaque instrument from the second imaging modality is an intra-operative image.

BRIEF DESCRIPTION OF THE FIGURES

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIGS. 2 and 3 illustrate a fluoroscopic image obtained from one specific pose. FIG. 4 illustrates a fluoroscopic image obtained in a different pose, as compared to FIGS. 2 and 3, as a result of C-arm rotation. The Bronchoscope —240, 340, 440, the instrument —210, 310, 410, ribs —220, 320, 420 and body boundary —230, 330, 430 are visible. The multi view pose estimation method uses the visible elements in FIGS. 2, 3, 4 as an input.

Figure 1:
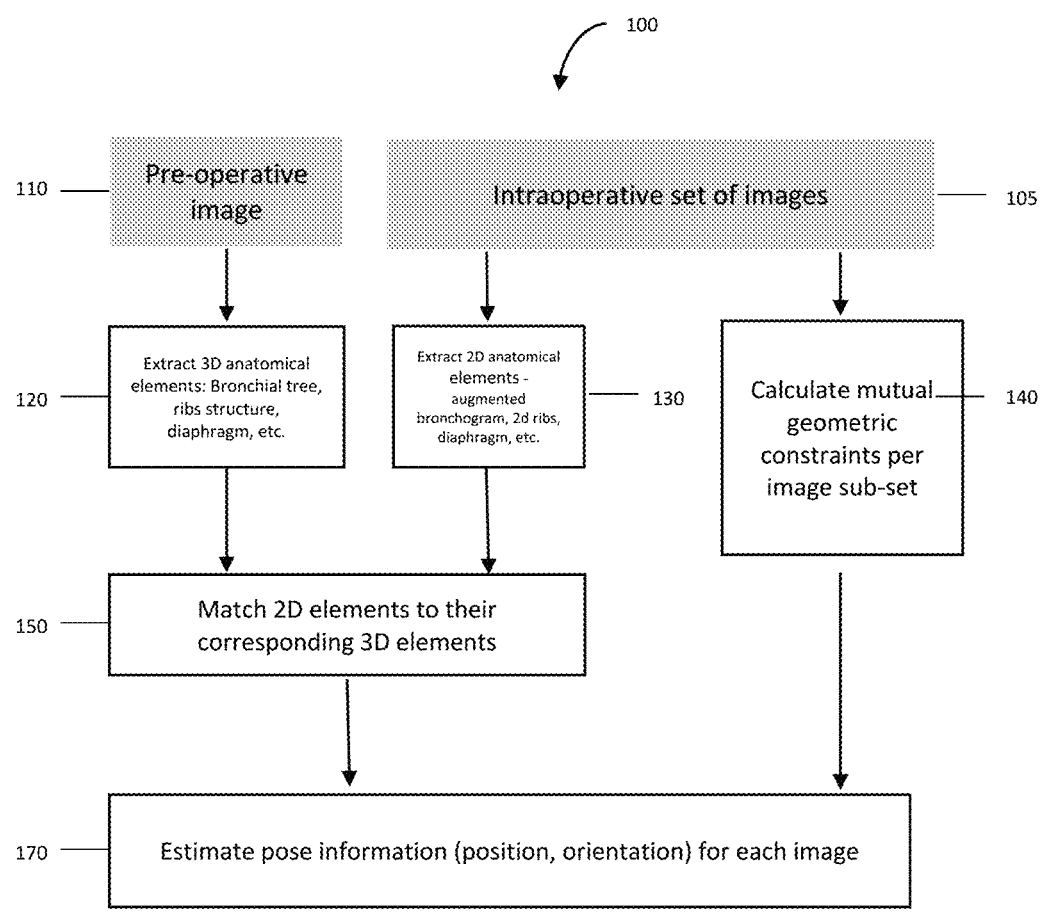
FIG. 1 shows a block diagram of a multi-view pose estimation method used in some embodiments of the method of the present invention.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiments, though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, a "plurality" refers to more than one in number, e.g., but not limited to, 2, 3, 4, 5, 6, 7, 8, 9, 10, etc. For example, a plurality of images can be 2 images, 3 images, 4 images, 5 images, 6 images, 7 images, 8 images, 9 images, 10 images, etc.

As used herein, an "anatomical element" refers to a landmark, which can be, e.g.: an area of interest, an incision point, a bifurcation, a blood vessel, a bronchial airway, a rib or an organ.

As used herein, "geometrical constraints" or "geometric constraints" or "mutual constraints" or "mutual geometric constraints" refer to a geometrical relationship between physical organs (e.g., at least two physical organs) in a subject's body which construct a similar geometric relationship within the subject between ribs, the boundary of the body, etc. Such geometrical relationships, as being observed through different imaging modalities, either remain unchanged or their relative movement can be neglected or quantified.

As used herein, a "pose" refers to a set of six parameters that determine a relative position and orientation of the intraoperative imaging device source as a substitute to the optical camera device. As a non-limiting example, a pose can be obtained as a combination of relative movements between the device, patient bed, and the patient. Another non-limiting example of such movement is the rotation of the intraoperative imaging device combined with its movement around the static patient bed with static patient on the bed.

As used herein, a "position" refers to the location (that can be measured in any coordinate system such as x, y, and z Cartesian coordinates) of any object, including an imaging device itself within a 3D space.

As used herein, an "orientation" refers the angles of the intraoperative imaging device. As non-limiting examples, the intraoperative imaging device can be oriented facing upwards, downwards, or laterally.

As used herein, a "pose estimation method" refers to a method to estimate the parameters of a camera associated with a second imaging modality within the 3D space of the first imaging modality. A non-limiting example of such a method is to obtain the parameters of the intraoperative fluoroscopic camera within the 3D space of a preoperative CT. A mathematical model uses such estimated pose to project at least one 3D point inside of a preoperative computed tomography (CT) image to a corresponding 2D point inside the intraoperative X-ray image.

As used herein, a "multi view pose estimation method" refers a method to estimate to poses of at least two different poses of the intraoperative imaging device. Where the imaging device acquires image from the same scene/subject.

As used herein, "relative angular difference" refers to the angular difference of the between two poses of the imaging device caused by their relative angular movement.

As used herein, "relative pose difference" refers to both location and relative angular difference between two poses of the imaging device caused by the relative spatial movement between the subject and the imaging device.

As used herein, "epipolar distance" refers to a measurement of the distance between a point and the epipolar line of the same point in another view. As used herein, an "epipolar line" refers to a calculation from an x, y vector or two-column matrix of a point or points in a view.

As used herein, a "similarity measure" refers to a real-valued function that quantifies the similarity between two objects.

In some embodiments, the present invention provides a method, comprising:
  obtaining a first image from a first imaging modality,
  extracting at least one element from the first image from the first imaging modality,
    wherein the at least one element comprises an airway, a blood vessel, a body cavity, or any combination thereof;
  obtaining, from a second imaging modality, at least (i) a first image of a radiopaque instrument in a first pose and (ii) a second image of the radiopaque instrument in a second pose,
    wherein the radiopaque instrument is in a body cavity of a patient;
  generating at least two augmented bronchograms,
    wherein a first augmented bronchogram corresponds to the first image of the radiopaque instrument in the first pose, and
    wherein a second augmented bronchogram corresponds to the second image of the radiopaque instrument in the second pose,
  determining mutual geometric constraints between:
    (i) the first pose of the radiopaque instrument, and
    (ii) the second pose of the radiopaque instrument,
  estimating the first pose of the radiopaque instrument and the second pose of the radiopaque instrument by comparing the first pose of the radiopaque instrument and the second pose of the radiopaque instrument to the first image of the first imaging modality,
    wherein the comparing is performed using:
      (i) the first augmented bronchogram,
      (ii) the second augmented bronchogram, and
      (iii) the at least one element, and
    wherein the estimated first pose of the radiopaque instrument and the estimated second pose of the radiopaque instrument meets the determined mutual geometric constraints,
  generating a third image; wherein the third image is an augmented image derived from the second imaging modality which highlights an area of interest, wherein the area of interest is determined from data from the first imaging modality.

In some embodiments, the at least one element from the first image from the first imaging modality further comprises a rib, a vertebra, a diaphragm, or any combination thereof. In some embodiments, the mutual geometric constraints are generated by:
  a. estimating a difference between (i) the first pose and (ii) the second pose by comparing the first image of the radiopaque instrument and the second image of the radiopaque instrument,
      wherein the estimating is performed using a device comprising a protractor, an accelerometer, a gyroscope, or any combination thereof, and wherein the device is attached to the second imaging modality;
  b. extracting a plurality of image features to estimate a relative pose change,
      wherein the plurality of image features comprise anatomical elements, non-anatomical elements, or any combination thereof,
      wherein the image features comprise: patches attached to a patient, radiopaque markers positioned in a field of view of the second imaging modality, or any combination thereof,
      wherein the image features are visible on the first image of the radiopaque instrument and the second image of the radiopaque instrument;
  c. estimating a difference between (i) the first pose and (ii) the second pose by using a at least one camera,
      wherein the camera comprises: a video camera, an infrared camera, a depth camera, or any combination thereof,
      wherein the camera is at a fixed location,
      wherein the camera is configured to track at least one feature,
        wherein the at least one feature comprises: a marker attached the patient, a marker attached to the second imaging modality, or any combination thereof, and
        tracking the at least one feature;
  d. or any combination thereof.

In some embodiments, the method further comprises: tracking the radiopaque instrument for: identifying a trajectory, and using the trajectory as a further geometric constraint, wherein the radiopaque instrument comprises an endoscope, an endo-bronchial tool, or a robotic arm.

In some embodiments, the present invention is a method, comprising:
  generating a map of at least one body cavity of the patient,
    wherein the map is generated using a first image from a first imaging modality, obtaining, from a second imaging modality, an image of a radiopaque instrument comprising at least two attached markers,
    wherein the at least two attached markers are separated by a known distance, identifying a pose of the radiopaque instrument from the second imaging modality relative to a map of at least one body cavity of a patient,
  identifying a first location of the first marker attached to the radiopaque instrument on the second image from the second imaging modality,
  identifying a second location of the second marker attached to the radiopaque instrument on the second image from the second imaging modality, and
  measuring a distance between the first location of the first marker and the second location of the second marker, projecting the known distance between the first marker and the second marker, comparing the measured distance with the projected known distance between the first marker and the second marker to identify a specific location of the radiopaque instrument inside the at least one body cavity of the patient.

In some embodiments, the radiopaque instrument comprises an endoscope, an endo-bronchial tool, or a robotic arm.

In some embodiments, the method further comprises: identifying a depth of the radiopaque instrument by use of a trajectory of the radiopaque instrument.

In some embodiments, the first image from the first imaging modality is a pre-operative image. In some embodiments, the at least one image of the radiopaque instrument from the second imaging modality is an intra-operative image.

In some embodiments, the present invention is a method, comprising:

obtaining a first image from a first imaging modality,
extracting at least one element from the first image from the first imaging modality,
  wherein the at least one element comprises an airway, a blood vessel, a body cavity or any combination thereof;
obtaining, from a second imaging modality, at least (i) a one image of a radiopaque instrument and (ii) another image of the radiopaque instrument in two different poses of second imaging modality
  wherein the first image of the radiopaque instrument is captured at a first pose of second imaging modality,
  wherein the second image of the radiopaque instrument is captured at a second pose of second imaging modality, and
  wherein the radiopaque instrument is in a body cavity of a patient;
generating at least two augmented bronchograms correspondent to each of two poses of the imaging device,
  wherein a first augmented bronchogram derived from the first image of the radiopaque instrument and the second augmented bronchogram derived from the second image of the radiopaque instrument,
determining mutual geometric constraints between:
  (i) the first pose of the second imaging modality, and
  (ii) the second pose of the second imaging modality,
estimating the two poses of the second imaging modality relatively to the first image of the first imaging modality, using the correspondent augmented bronchogram images and at least one element extracted from the first image of the first imaging modality;
  wherein the two estimated poses satisfy the mutual geometric constrains.
generating a third image; wherein the third image is an augmented image derived from the second imaging modality highlighting the area of interest, based on data sourced from the first imaging modality.

In some embodiments, anatomical elements such as: a rib, a vertebra, a diaphragm, or any combination thereof, are extracted from the first imaging modality and from the second imaging modality.

In some embodiments, the mutual geometric constraints are generated by:

a. estimating a difference between (i) the first pose and (ii) the second pose by comparing the first image of the radiopaque instrument and the second image of the radiopaque instrument,
  wherein the estimating is performed using a device comprising a protractor, an accelerometer, a gyroscope, or any combination thereof, and
  wherein the device is attached to the second imaging modality;
b. extracting a plurality of image features to estimate a relative pose change,
  wherein the plurality of image features comprise anatomical elements, non-anatomical elements, or any combination thereof,
  wherein the image features comprise: patches attached to a patient, radiopaque markers positioned in a field of view of the second imaging modality, or any combination thereof,
  wherein the image features are visible on the first image of the radiopaque instrument and the second image of the radiopaque instrument;
c. estimate a difference between (i) the first pose and (ii) the second pose by using a at least one camera,
  wherein the camera comprises: a video camera, an infrared camera, a depth camera, or any combination thereof,
  wherein the camera is at a fixed location,
  wherein the camera is configured to track at least one feature,
    wherein the at least one feature comprises: a marker attached the patient, a marker attached to the second imaging modality, or any combination thereof, and
  tracking the at least one feature;
d. or any combination thereof.

In some embodiments, the method further comprises tracking the radiopaque instrument to identify a trajectory and using such trajectory as additional geometric constrains, wherein the radiopaque instrument comprises an endoscope, an endo-bronchial tool, or a robotic arm.

In some embodiments, the present invention is a method to identify the true instrument location inside the patient, comprising:

using a map of at least one body cavity of a patient generated from a first image of a first imaging modality,
obtaining, from a second imaging modality, an image of the radiopaque instrument with at least two markers attached to it and having the defined distance between them, that may be perceived from the image as located in at least two different body cavities inside the patient,
obtaining the pose of the second imaging modality relative to the map
identifying a first location of the first marker attached to the radiopaque instrument on the second image from the second imaging modality,
identifying a second location of the second marker attached to the radiopaque instrument on the second image from the second imaging modality, and
measuring a distance between the first location of the first marker and the second location of the second marker.
projecting the known distance between markers on each of the perceived location of the radiopaque instrument using the pose of the second imaging modality
comparing the measured distance to each of projected distances between the two markers to identify the true instrument location inside the body.

In some embodiments, the radiopaque instrument comprises an endoscope, an endo-bronchial tool, or a robotic arm.

In some embodiments, the method further comprises: identifying a depth of the radiopaque instrument by use of a trajectory of the radiopaque instrument.

In some embodiments, the first image from the first imaging modality is a pre-operative image. In some embodiments, the at least one image of the radiopaque instrument from the second imaging modality is an intra-operative image.

Multi View Pose Estimation

The application PCT/IB2015/000438 includes a description of a method to estimate the pose information (e.g., position, orientation) of a fluoroscope device relative to a patient during an endoscopic procedure, and is herein incorporated by reference in its entirety. PCT/IB15/002148 filed Oct. 20, 2015 is also herein incorporated by reference in its entirety.

Figure 3:
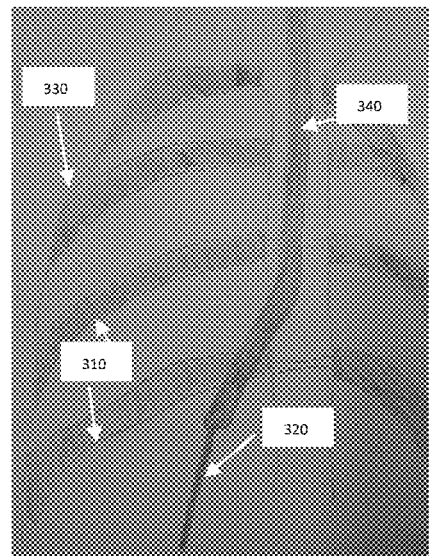
Figure 4:
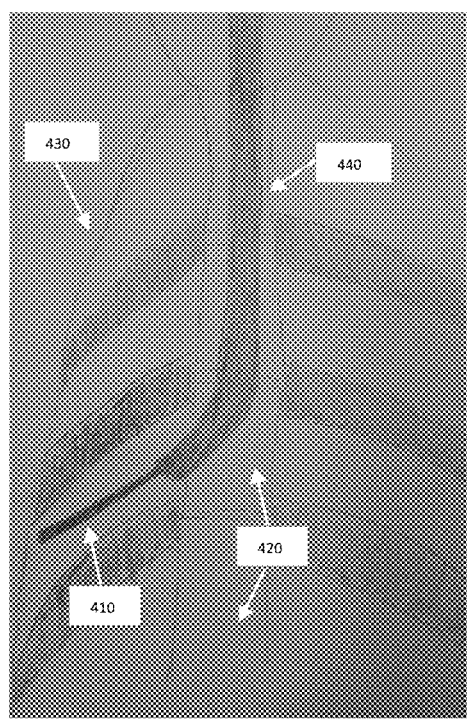
Figure 5:
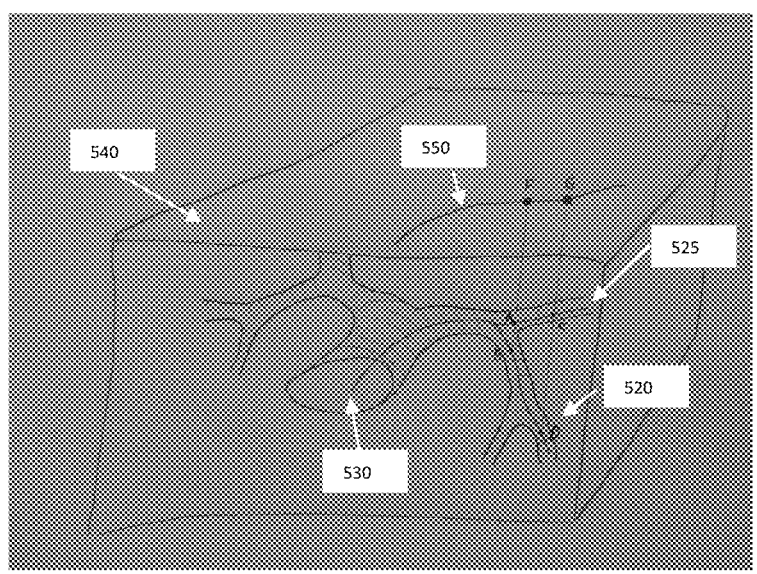
FIG. 5 shows a schematic drawing of the structure of bronchial airways as utilized in the method of the present invention. The airways centerlines are represented by 530. A catheter is inserted into the airways structure and imaged by a fluoroscopic device with an image plane 540. The catheter projection on the image is illustrated by the curve 550 and the radio opaque markers attached to it are projected into points G and F.

The present invention is a method which includes data extracted from a set of intra-operative images, where each of the images is acquired in at least one (e.g., 1, 2, 3, 4, etc.) unknown pose obtained from an imaging device. These images are used as input for the pose estimation method. As an exemplary embodiment, FIGS. 3, 4, 5, are examples of a set of 3 Fluoroscopic images. The images in FIGS. 4 and 5 were acquired in the same unknown pose while the image in FIG. 3 was acquired in a different unknown pose. This set, for example, may or may not contain additional known positional data related to the imaging device. For example, a set may contain positional data, such as C-arm location and orientation, which can be provided by a Fluoroscope or acquired through a measurement device attached to the Fluoroscope, such as protractor, accelerometer, gyroscope, etc.

In some embodiments, anatomical elements are extracted from additional intraoperative images and these anatomical elements imply geometrical constraints which can be introduced into the pose estimation method. As a result, the number of elements extracted from a single intraoperative image can be reduced prior to using the pose estimation method.

In some embodiments, the multi view pose estimation method further includes overlaying information sourced from a pre-operative modality over any image from the set of intraoperative images.

In some embodiments, a description of overlaying information sourced from a pre-operative modality over intraoperative images can be found in PCT/IB2015/000438, which is incorporated herein by reference in its entirety.

In some embodiments, the plurality of second imaging modalities allow for changing a Fluoroscope pose relatively to the patient (e.g., but not limited to, a rotation or linear movement of the Fluoroscope arm, patient bed rotation and movement, patient relative movement on the bed, or any combination of the above) to obtain the plurality of images, where the plurality of images are obtained from abovementioned relative poses of the fluoroscopic source as any combination of rotational and linear movement between the patient and Fluoroscopic device.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

Reference is now made to the following examples, which together with the above descriptions illustrate some embodiments of the invention in a non limiting fashion.

Example: Minimally Invasive Pulmonary Procedure

Figure 2:
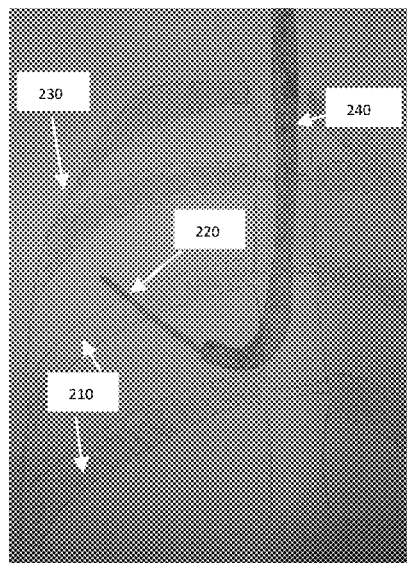
FIGS. 2, 3, and 4 show an exemplary embodiments of intraoperative images used in the method of the present invention.
Figure 6:
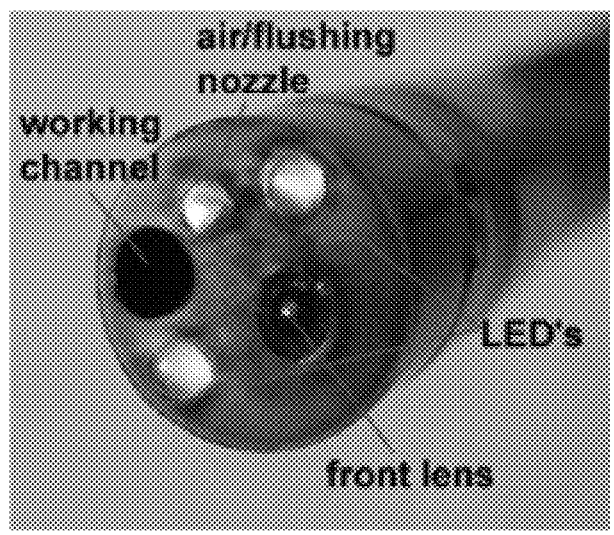
FIG. 6 is an image of a bronchoscopic device tip attached to a bronchoscope, in which the bronchoscope can be used in an embodiment of the method of the present invention.

A non-limiting exemplary embodiment of the present invention can be applied to a minimally invasive pulmonary procedure, where endo-bronchial tools are inserted into bronchial airways of a patient through a working channel of the Bronchoscope (see FIG. 6). Prior to commencing a diagnostic procedure, the physician performs a Setup process, where the physician places a catheter into several (e.g., 2, 3, 4, etc.) bronchial airways around an area of interest. The Fluoroscopic images are acquired for every location of the endo-bronchial catheter, as shown in FIGS. 2, 3, and 4. An example of the navigation system used to perform the pose estimation of the intra-operative Fluoroscopic device is described in application PCT/IB2015/000438, and the present method of the invention uses the extracted elements (e.g., but not limited to, multiple catheter locations, rib anatomy, and a patient's body boundary).

After estimating the pose in the area of interest, pathways for inserting the bronchoscope can be identified on a pre-procedure imaging modality, and can be marked by highlighting or overlaying information from a pre-operative image over the intraoperative Fluoroscopic image. After navigating the endo-bronchial catheter to the area of interest, the physician can rotate, change the zoom level, or shift the Fluoroscopic device for, e.g., verifying that the catheter is located in the area of interest. Typically, such pose changes of the Fluoroscopic device, as illustrated by FIG. 4, would invalidate the previously estimated pose and require that the physician repeats the Setup process. However, since the catheter is already located inside the potential area of interest, repeating the Setup process need not be performed.

FIG. 4 shows an exemplary embodiment of the present invention, showing the pose of the Fluoroscope angle being estimated using anatomical elements, which were extracted from FIGS. 2 and 3 (in which, e.g., FIGS. 2 and 3 show images obtained from the initial Setup process and the additional anatomical elements extracted from image, such as catheter location, ribs anatomy and body boundary). The pose can be changed by, for example, (1) moving the Fluoroscope (e.g., rotating the head around the c-arm), (2) moving the Fluoroscope forward are backwards, or alternatively through the subject position change or either through the combination of both etc. In addition, the mutual geometric constraints between FIG. 2 and FIG. 4, such as positional data related to the imaging device, can be used in the estimation process.

FIG. 1 is an exemplary embodiment of the present invention, and shows the following:

I. The component 120 extracts 3D anatomical elements, such as Bronchial airways, ribs, diaphragm, from the pre-operative image, such as, but not limited to, CT, magnetic resonance imaging (MM), Positron emission tomography-computed tomography (PET-CT), using an automatic or semi-automatic segmentation process, or any combination thereof. Examples of automatic or semi-automatic segmentation processes are described in "Three-dimensional Human Airway Segmentation Methods for Clinical Virtual Bronchoscopy", Atilla P. Kiraly, William E. Higgins, Geoffrey McLennan, Eric A. Hoffman, Joseph M. Reinhardt, which is hereby incorporated by reference in its entirety.

II. The component 130 extracts 2D anatomical elements (which are further shown in FIG. 4, such as Bronchial airways 410, ribs 420, body boundary 430 and diaphragm) from a set of intraoperative images, such as, but not limited to, Fluoroscopic images, ultrasound images, etc.

III. The component 140 calculates the mutual constraints between each subset of the images in the set of intraoperative images, such as relative angular difference, relative pose difference, epipolar distance, etc.

In another embodiment, the method includes estimating the mutual constraints between each subset of the images in the set of intraoperative images. Non-limiting examples of such methods are: (1) the use of a measurement device attached to the intraoperative imaging device to estimate a relative pose change between at least two poses of a pair of fluoroscopic images. (2) The extraction of image features, such as anatomical elements or non-anatomical elements including, but not limited to, patches (e.g., ECG patches) attached to a patient or radiopaque markers positioned inside the field of view of the intraoperative imaging device, that are visible on both images, and using these features to estimate the relative pose change. (3) The use of a set of cameras, such as video camera, infrared camera, depth camera, or any combination of those, attached to the specified location in the procedure room, that tracks features, such as patches attached to the patient or markers, markers attached to imaging device, etc. By tracking such features the component can estimate the imaging device relative pose change.

IV. The component 150 matches the 3D element generated from preoperative image to their corresponding 2D elements generated from intraoperative image. For example, matching a given 2D Bronchial airway extracted from Fluoroscopic image to the set of 3D airways extracted from the CT image.

V. The component 170 estimates the poses for the each of the images in the set of intra-operative images in the desired coordinate system, such as preoperative image coordinate system, operation environment related, coordinated system formed by other imaging or navigation device, etc.

The inputs to this component are as follows:

3D anatomical elements extracted from the patient preoperative image.

2D anatomical elements extracted from the set of intraoperative images. As stated herein, the images in the set can be sourced from the same or different imaging device poses.

Mutual constraints between each subset of the images in the set of intraoperative images The component 170 evaluates the pose for each image from the set of intra-operative images such that:

The 2D extracted elements match the correspondent and projected 3D anatomical elements.

The mutual constraint conditions 140 apply for the estimated poses.

To match the projected 3D elements, sourcing a preoperative image to the correspondent 2D elements from an inter-operative image, a similarity measure, such as a distance metric, is needed. Such a distance metric provides a measure to assess the distances between the projected 3D elements and their correspondent 2D elements. For example, a Euclidian distance between 2 polylines (e.g., connected sequence of line segments created as a single object) can be used as a similarity measure between 3D projected Bronchial airway sourcing pre-operative image to 2D airway extracted from the intra-operative image.

Additionally, in an embodiment of the method of the present invention, the method includes estimating a set of poses that correspond to a set of intraoperative images by identifying such poses which optimize a similarity measure, provided that the mutual constraints between the subset of images from intraoperative image set are satisfied. The optimization of the similarity measure can be referred to as a Least Squares problem and can be solved in several methods, e.g., (1) using the well-known bundle adjustment algorithm which implements an iterative minimization method for pose estimation, and which is herein incorporated by reference in its entirety: B. Triggs; P. McLauchlan; R. Hartley; A. Fitzgibbon (1999) "Bundle Adjustment—A Modern Synthesis". *ICCV '99: Proceedings of the International Workshop on Vision Algorithms*. Springer-Verlag. pp. 298-372, and (2) using a grid search method to scan the parameter space in search for optimal poses that optimize the similarity measure.

Markers

Radio-opaque markers can be placed in predefined locations on the medical instrument in order to recover 3D information about the instrument position. Several pathways of 3D structures of intra-body cavities, such as bronchial airways or blood vessels, can be projected into similar 2D curves on the intraoperative image. The 3D information obtained with the markers may be used to differentiate between such pathways, as shown, e.g., in Application PCT/IB2015/000438.

In an exemplary embodiment of the present invention, as illustrated by FIG. 5, an instrument is imaged by an intraoperative device and projected to the imaging plane 505. It is unknown whether the instrument is placed inside pathway 520 or 525 since both pathways are projected into the same curve on the image plane 505. In order to differentiate between pathway 520 and 525, it is possible to use at least 2 radiopaque markers attached to the catheter having predefined distance "m" between the markers. In FIG. 5, the markers observed on the preoperative image are named "G" and "F".

The differentiation process between 520 and 525 can be performed as follows:

(1) Project point F from intraoperative image on the potential candidates of correspondent airways 520, 525 to obtain A and B points.

(2) Project point G from intraoperative image on the potential candidates of correspondent airways 520, 525 to obtain points C and D.

(3) Measure the distance between pairs of projected markers |AC| and |BD|.

(4) Compare the distances |AC| on 520 and |BD| on 525 to the distance m predefined by tool manufacturer. Choose appropriate airway according to a distance similarity.

Tracked Scope

Figure 7:
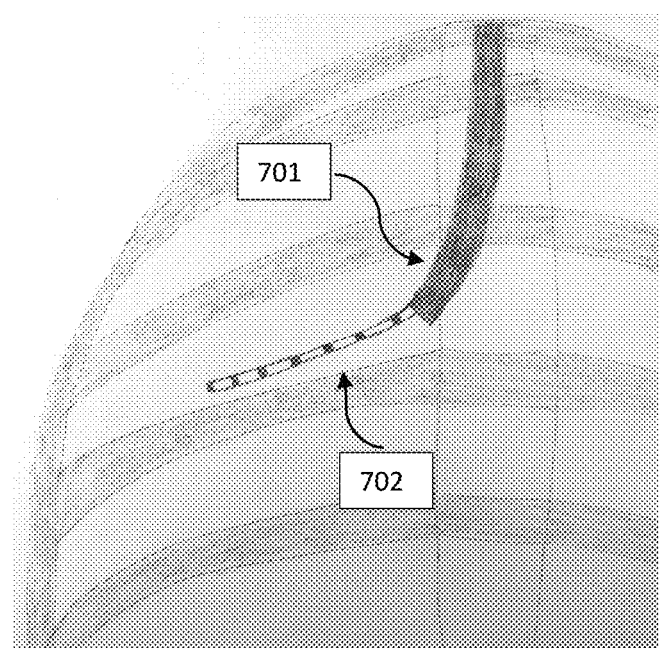
FIG. 7 is an illustration according to an embodiment of the method of the present invention, where the illustration is of a fluoroscopic image of a tracked scope (701) used in a bronchoscopic procedure with an operational tool (702) that extends from it. The operational tool may contain radio opaque markers or unique pattern attached to it.

As non-limiting examples, methods to register a patient CT scan with a Fluoroscopic device are disclosed herein. This method uses anatomical elements detected both in the Fluoroscopic image and in the CT scan as an input to a pose estimation algorithm that produces a Fluoroscopic device Pose (e.g., orientation and position) with respect to the CT scan. The following extends this method by adding 3D space trajectories, corresponding to an endo-bronchial device position, to the inputs of the registration method. These trajectories can be acquired by several means, such as: attaching positional sensors along a scope or by using a robotic endoscopic arm. Such an endo-bronchial device will be referred from now on as Tracked Scope. The Tracked scope is used to guide operational tools that extends from it to the target area (see FIG. 7). The diagnostic tools may be a catheter, forceps, needle, etc. The following describes how to use positional measurements acquired by the Tracked scope to improve the accuracy and robustness of the registration method shown herein.

In one embodiment, the registration between Tracked Scope trajectories and coordinate system of Fluoroscopic device is achieved through positioning of the Tracked Scope in various locations in space and applying a standard pose estimation algorithm. See the following paper for a reference to a pose estimation algorithm: F. Moreno-Noguer, V. Lepetit and P. Fua in the paper "EPnP: Efficient Perspective-n-Point Camera Pose Estimation", which is hereby incorporated by reference in its entirety.

The pose estimation method disclosed herein is performed through estimating a Pose in such way that selected elements in the CT scan are projected on their corresponding elements in the fluoroscopic image. In one embodiment of the current invention, adding the Tracked Scope trajectories as an input to the pose estimation method extends this method. These trajectories can be transformed into the Fluoroscopic device coordinate system using the methods herein. Once transformed to the Fluoroscopic device coordinate system, the trajectories serve as additional constraints to the pose estimation method, since the estimated pose is constrained by the condition that the trajectories must fit the bronchial airways segmented from the registered CT scan.

The Fluoroscopic device estimated Pose may be used to project anatomical elements from the pre-operative CT to the Fluoroscopic live video in order to guide an operational tool to a specified target inside the lung. Such anatomical elements may be, but are not limited to: a target lesion, a pathway to the lesion, etc. The projected pathway to the target lesion provides the physician with only two-dimensional information, resulting in a depth ambiguity, that is to say several airways segmented on CT may correspond to the same projection on the 2D Fluoroscopic image. It is important to correctly identify the bronchial airway on CT in which the operational tool is placed. One method used to reduce such ambiguity, described herein, is performed by using radiopaque markers placed on the tool providing depth information. In another embodiment of the current invention, the Tracked scope may be used to reduce such ambiguity since it provides the 3D position inside the bronchial airways. Having such approach applied to the brunching bronchial tree, it allows eliminating the potential ambiguity options until the Tracked Scope tip 701 on FIG. 7. Assuming the operational tool 702 on FIG. 7 does not have the 3D trajectory, although the abovementioned ambiguity may still happen for this portion 702 of the tool, such event is much less probable to occur. Therefore this embodiment of current invention improves the ability of the method described herein to correctly identify the current tool's position.

EQUIVALENTS

The present invention provides among other things novel methods and compositions for treating mild to moderate acute pain and/or inflammation. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entireties as if each individual publication or patent was specifically and individually indicated to be incorporated by reference.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A method, comprising:
obtaining a first image from a first imaging modality,
extracting at least one element from the first image from the first imaging modality, wherein the at least one element comprises an airway, a blood vessel, a body cavity, or any combination thereof;
obtaining, from a second imaging modality, at least (i) a first image of a radiopaque instrument in a first pose of second imaging modality and (ii) a second image of the radiopaque instrument in a second pose of second imaging modality,
wherein the radiopaque instrument is in a body cavity of a patient;
generating at least two augmented bronchograms,
wherein a first augmented bronchogram corresponds to the first image of the second imaging modality in the first pose, and
wherein a second augmented bronchogram corresponds to the second image of the second imaging modality in the second pose,
determining mutual geometric constraints between:
(i) the first pose of the of second imaging modality, and
(ii) the second pose of the of second imaging modality,
estimating the first pose of the of second imaging modality and the second pose of the of second imaging modality,
wherein the estimation is performed using:
(i) the first augmented bronchogram,
(ii) the second augmented bronchogram, and
(iii) the at least one element, and
wherein the estimated first pose of the of second imaging modality and the estimated second pose of the of second imaging modality meets the determined mutual geometric constraints,
generating a third image; wherein the third image is an augmented image derived from the second imaging modality which highlights an area of interest,
wherein the area of interest is determined from projecting data from the estimated first pose and the estimated second pose.

2. The method of claim 1, wherein there is additional element from the first image from the first imaging modality and second image of second imaging modality further comprises a rib, a vertebra, a diaphragm, or any combination thereof.

3. The method of claim 1, wherein the mutual geometric constraints are generated by:
a. estimating a difference between (i) the first pose and (ii) the second pose by comparing the first image of the radiopaque instrument and the second image of the radiopaque instrument,
wherein the estimating is performed using a device comprising a protractor, an accelerometer, a gyroscope, or any combination thereof, and wherein the device is attached to the second imaging modality;

b. extracting a plurality of image features to estimate a relative pose change,
   wherein the plurality of image features comprise anatomical elements, non-anatomical elements, or any combination thereof,
   wherein the image features comprise: patches attached to a patient, radiopaque markers positioned in a field of view of the second imaging modality, or any combination thereof,
   wherein the image features are visible on the first image of the radiopaque instrument and the second image of the radiopaque instrument;
c. estimating a difference between (i) the first pose and (ii) the second pose by using a at least one camera,
   wherein the camera comprises: a video camera, an infrared camera, a depth camera, or any combination thereof,
   wherein the camera is at a fixed location,
   wherein the camera is configured to track at least one feature, wherein the at least one feature comprises: a marker attached the patient, a marker attached to the second imaging modality, or any combination thereof, and
   tracking the at least one feature;
d. or any combination thereof.

4. The method of claim 1, further comprising: tracking the radiopaque instrument for:
   identifying a trajectory, and
   using the trajectory as a further geometric constraint,
   wherein the radiopaque instrument comprises an endoscope, an endo-bronchial tool, or a robotic arm.

5. The method of claim 1, wherein the first image from the first imaging modality is a pre-operative image.

6. The method of claim 1, wherein the at least one image of the radiopaque instrument from the second imaging modality is an intra-operative image.

* * * * *